United States Patent
Baril et al.

(10) Patent No.: US 11,864,953 B2
(45) Date of Patent: Jan. 9, 2024

(54) SMOKE EVACUATING TISSUE GUARD FOR TISSUE REMOVAL AND OTHER SURGICAL PROCEDURES

(71) Applicant: Covidien LP, Mansfield, MA (US)

(72) Inventors: Jacob C. Baril, North Haven, CT (US); Matthew A. Dinino, North Haven, CT (US); Saumya Banerjee, North Haven, CT (US)

(73) Assignee: COVIDIEN LP, Mansfield, MA (US)

( * ) Notice: Subject to any disclaimer, the term of this patent is extended or adjusted under 35 U.S.C. 154(b) by 1023 days.

(21) Appl. No.: 16/750,150

(22) Filed: Jan. 23, 2020

(65) Prior Publication Data

US 2021/0228305 A1    Jul. 29, 2021

(51) Int. Cl.
*A61M 39/02* (2006.01)
*A61B 90/00* (2016.01)
*A61B 18/00* (2006.01)
*A61B 17/34* (2006.01)

(52) U.S. Cl.
CPC ........ *A61B 90/05* (2016.02); *A61B 2017/348* (2013.01); *A61B 2018/00601* (2013.01); *A61B 2018/00744* (2013.01); *A61B 2218/008* (2013.01); *A61M 2039/022* (2013.01); *A61M 2039/0279* (2013.01)

(58) Field of Classification Search
CPC .............. A61B 90/05; A61B 2017/348; A61B 2018/00601; A61B 2018/00744; A61B 2218/008; A61B 17/3423; A61B 2090/401; A61B 90/40; A61M 2039/022; A61M 2039/0279; A61M 39/0247
See application file for complete search history.

(56) References Cited

U.S. PATENT DOCUMENTS

| | | | |
|---|---|---|---|
| 6,443,152 B1 | 9/2002 | Lockhart et al. | |
| 6,663,610 B1 | 12/2003 | Thompson et al. | |
| 7,201,882 B2 | 4/2007 | Cesa | |
| 8,088,289 B2 | 1/2012 | Tribelsky | |
| 8,424,518 B2 | 4/2013 | Smutney et al. | |
| 8,641,488 B1 * | 2/2014 | Shvetsov | A61B 18/203 606/4 |
| 2002/0103485 A1 | 8/2002 | Melnyk et al. | |

FOREIGN PATENT DOCUMENTS

EP    3307342 A1    4/2018

* cited by examiner

*Primary Examiner* — Amber R Stiles
*Assistant Examiner* — Phoebe Anne Staton
(74) *Attorney, Agent, or Firm* — Carter, DeLuca & Farrell LLP

(57) ABSTRACT

A smoke evacuating tissue guard includes a tubular body defining a longitudinally-extending passageway, a collar coupled to a proximal end portion of the tubular body, and an outlet coupled to the collar and in fluid communication with an annular channel defined through the collar. Upon application of suction through the smoke evacuating tissue guard, the smoke evacuating tissue guard establishes a fluid path extending from the passageway of the tubular body and into the annular channel of the collar via an annular gap defined between the tubular body and the collar.

17 Claims, 4 Drawing Sheets

SMOKE EVACUATING TISSUE GUARD FOR TISSUE REMOVAL AND OTHER SURGICAL PROCEDURES

FIELD

The present technology relates to tissue removal and, more particularly, to tissue guards and systems incorporating the same for use in tissue removal procedures requiring surgical smoke evacuation.

BACKGROUND

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total removal of tissue from an internal body cavity. However, the restricted access provided by minimally-invasive openings (natural passageways and/or surgically created openings) presents challenges with respect to maneuverability and visualization. The restricted access also presents challenges when large tissue specimens are required to be removed. As such, tissue specimens that are deemed too large for intact removal may be broken down into a plurality of smaller pieces to facilitate removal from the internal body cavity. When severing tissue or otherwise treating the tissue, surgical smoke may be generated, which may impair visualization and/or otherwise hinder a clinician.

SUMMARY

As used herein, the term "distal" refers to the portion that is described which is further from a user, while the term "proximal" refers to the portion that is being described which is closer to a user. As used herein, the terms parallel and perpendicular are understood to include relative configurations that are substantially parallel and substantially perpendicular up to about + or −15 degrees from true parallel and true perpendicular.

Further, any or all of the aspects described herein, to the extent consistent, may be used in conjunction with any or all of the other aspects described herein.

Provided in accordance with aspects of the present disclosure is a smoke evacuating tissue guard including a tubular body, a collar, and an outlet. The tubular body has an outwardly flared proximal end portion and a distal end portion and a longitudinally-extending passageway. The collar is attached to the proximal end portion of the tubular body and defines an annular channel. The collar includes an outer annular section, an inner annular section facing the passageway, and a lip extending radially inward from the inner annular section. The inner annular section of the collar is spaced from the proximal end portion of the tubular body to define a first gap therebetween. The lip is spaced from the proximal end portion of the tubular body to define a second gap therebetween. The outlet extends from the collar and defines an inner channel in fluid communication with the annular channel. The first gap is less than a diameter of the annular channel and the second gap, such that the smoke evacuation tissue guard is configured to establish a pressure differential in the first gap upon application of suction through the smoke evacuating tissue guard.

In aspects, the lip may extend perpendicular to a longitudinal axis defined by the passageway of the tubular body.

In aspects, the distal end portion of the tubular body may be flared outwardly and may include a plurality of segments. The segments may taper in a distal direction, such that adjacent segments define a gap therebetween that increases in width in a distal direction.

In aspects, the smoke evacuating tissue guard may further include a plurality of hooks coupled to the outer annular section of the collar. The hooks may be adapted to connect to a proximal rim of an access device.

In aspects, the first gap may extend circumferentially about the passageway.

In aspects, the annular channel may be in fluid communication with the passageway of the tubular body via the first and second gaps.

In aspects, the collar, the tubular body, and the outlet may be monolithically formed with one another as a single component.

In accordance with another aspect of the disclosure, a smoke evacuating tissue guard includes a tubular body, a ring-shaped collar, and an outlet coupled to the collar. The tubular body defines a longitudinally-extending passageway and includes an outwardly flared proximal end portion, an outwardly flared distal end portion, and an intermediate portion connecting the proximal and distal end portions. The collar defines an annular channel and includes an outer annular section extending from the proximal end portion of the tubular body, and an inner annular section facing the passageway. The inner annular section is spaced from the proximal end portion of the tubular body to define a first annular gap therebetween. The outlet defines an inner channel in fluid communication with the annular channel. The smoke evacuating guard is configured to establish a fluid path that extends from the passageway of the tubular body, into the annular channel via the first annular gap, and into the inner channel via the annular channel upon application of suction through the smoke evacuating tissue guard.

In aspects, the collar may further include a lip extending radially inward from the inner annular section.

In aspects, the lip may be spaced from the proximal end portion of the tubular body to define a second annular gap therebetween.

In aspects, the first annular gap may be less than a diameter of the annular channel and the second gap, such that the smoke evacuation tissue guard is configured to establish a pressure differential in the first annular gap upon application of suction through the smoke evacuating tissue guard.

In aspects, the lip may extend perpendicular to a longitudinal axis defined by the passageway of the tubular body.

In aspects, the distal end portion of the tubular body may include a plurality of segments that taper in a distal direction, such that adjacent segments define a gap therebetween that increases in width in a distal direction.

In aspects, the first annular gap may extend circumferentially about the passageway.

In aspects, the annular channel may be in fluid communication with the passageway of the tubular body via the first and second annular gaps.

BRIEF DESCRIPTION OF THE DRAWINGS

The above and other aspects and features of the present disclosure will become more apparent in light of the following detailed description when taken in conjunction with FIG. 1 is a perspective view illustrating a smoke evacuating tissue guard provided in accordance with aspects of the disclosure.

DETAILED DESCRIPTION

When using a bipolar electrosurgical pencil to dissect a tissue specimen for extraction, a significant amount of smoke plume may be generated. The smoke plume may be harmful to the surgeon and may obstruct the surgical field. The present disclosure provides a smoke evacuating, tissue-cutting guard designed to remove smoke from the surgical site as rapidly as possible. The tissue guard implements unique principles taken from the Venturi Flow Equation to maximize the air evacuated while minimizing the noise produced via turbulence. The tissue guard has specific ratios of cross sectional area to maximize the evacuation. Due to the Venturi flow through the tissue guard, the tissue guard generates a negative pressure in two locations (e.g., proximally and distally) to maximize smoke evacuation. Further, the tissue guard may prevent smoke accumulation in a specimen bag as well as above the surgical site by evacuating smoke from both areas. The tissue guard has a relatively large distal opening and a proximal end having an inner diameter sized to shift the pressure/volume ratio. The pressure differential at a necked-down section of the tissue guard forces a mixing or multi-directional pull of the system.

Figure 1:
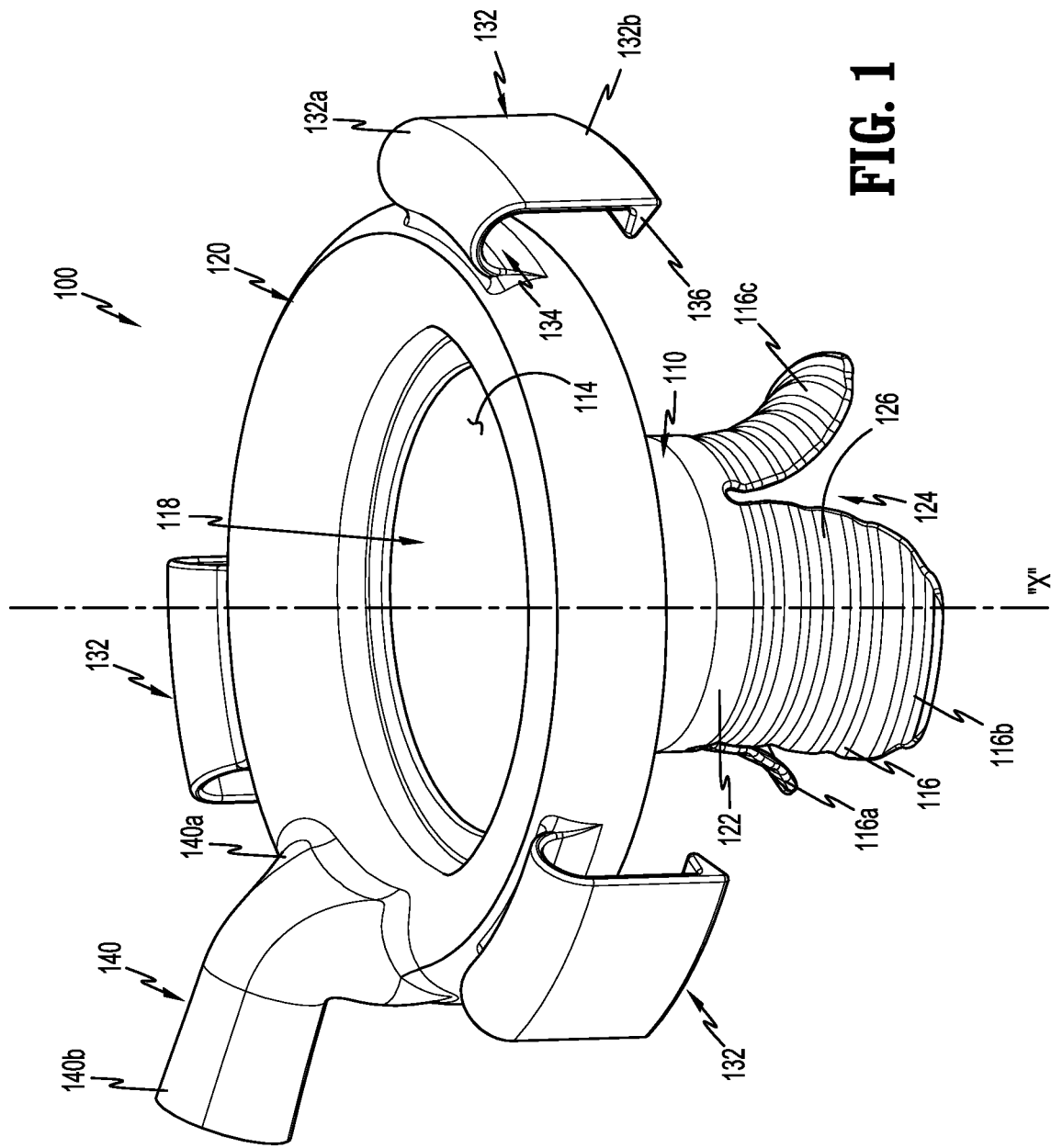
Figure 2:
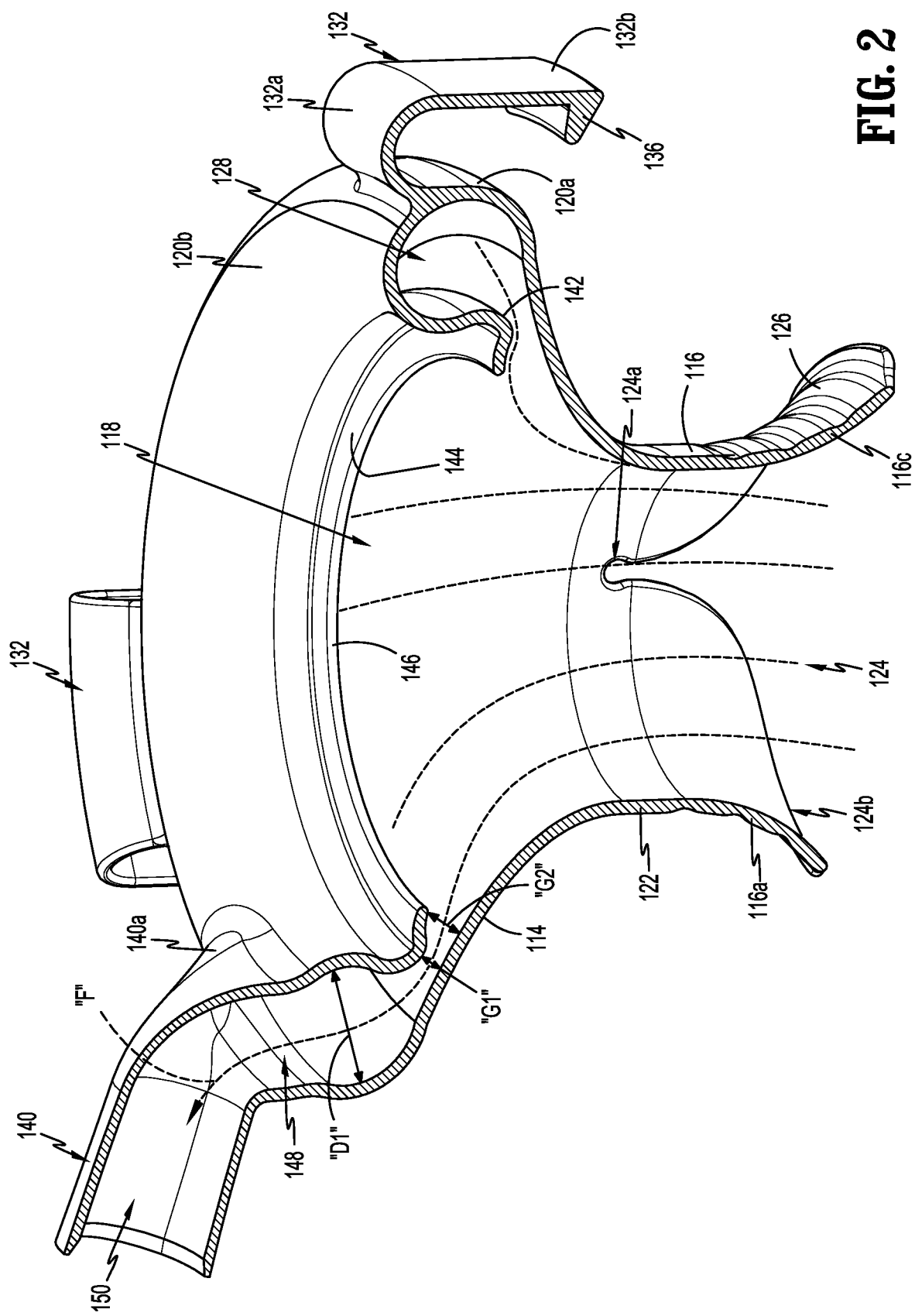
FIG. 2 is a longitudinal cross-sectional view illustrating the smoke evacuating tissue guard of FIG. 1.
Figure 3:
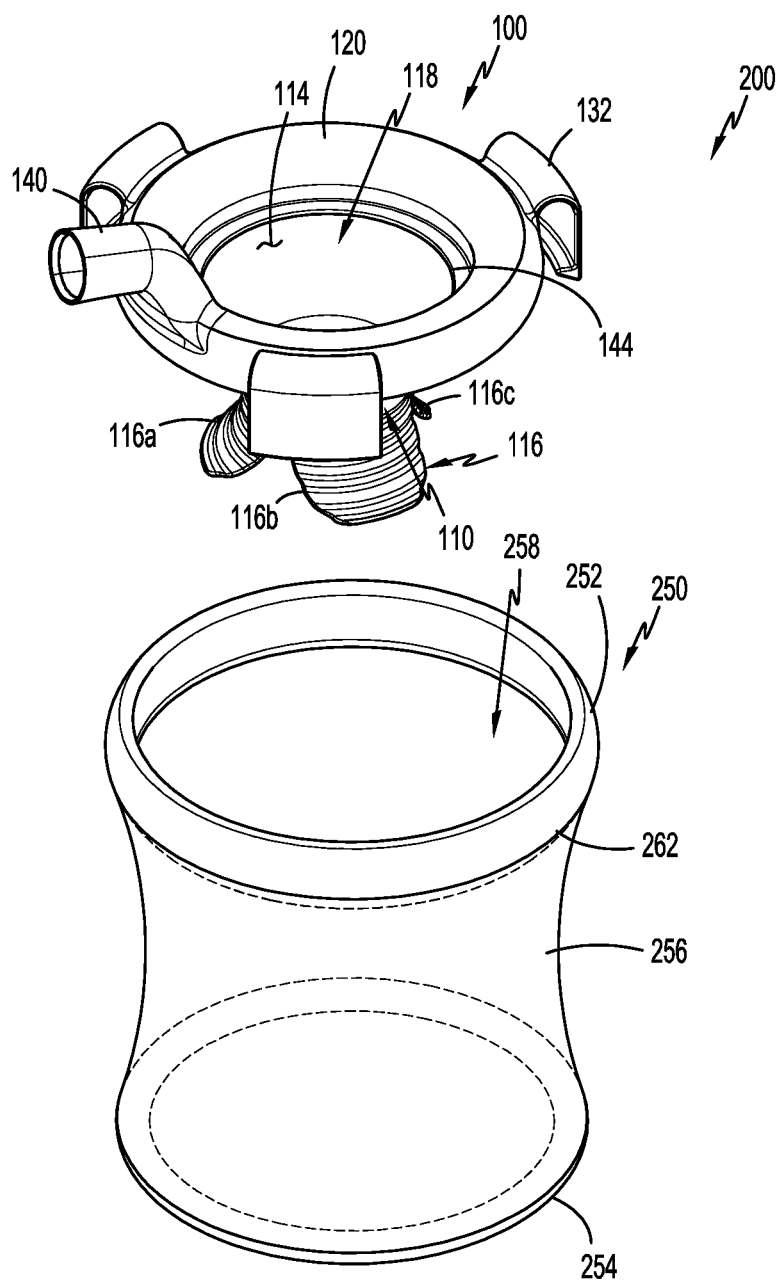
FIG. 3 is an exploded, top, perspective view of a system provided in accordance with the present disclosure including an access device and the smoke evacuating tissue guard of FIG. 1.
Figure 4:
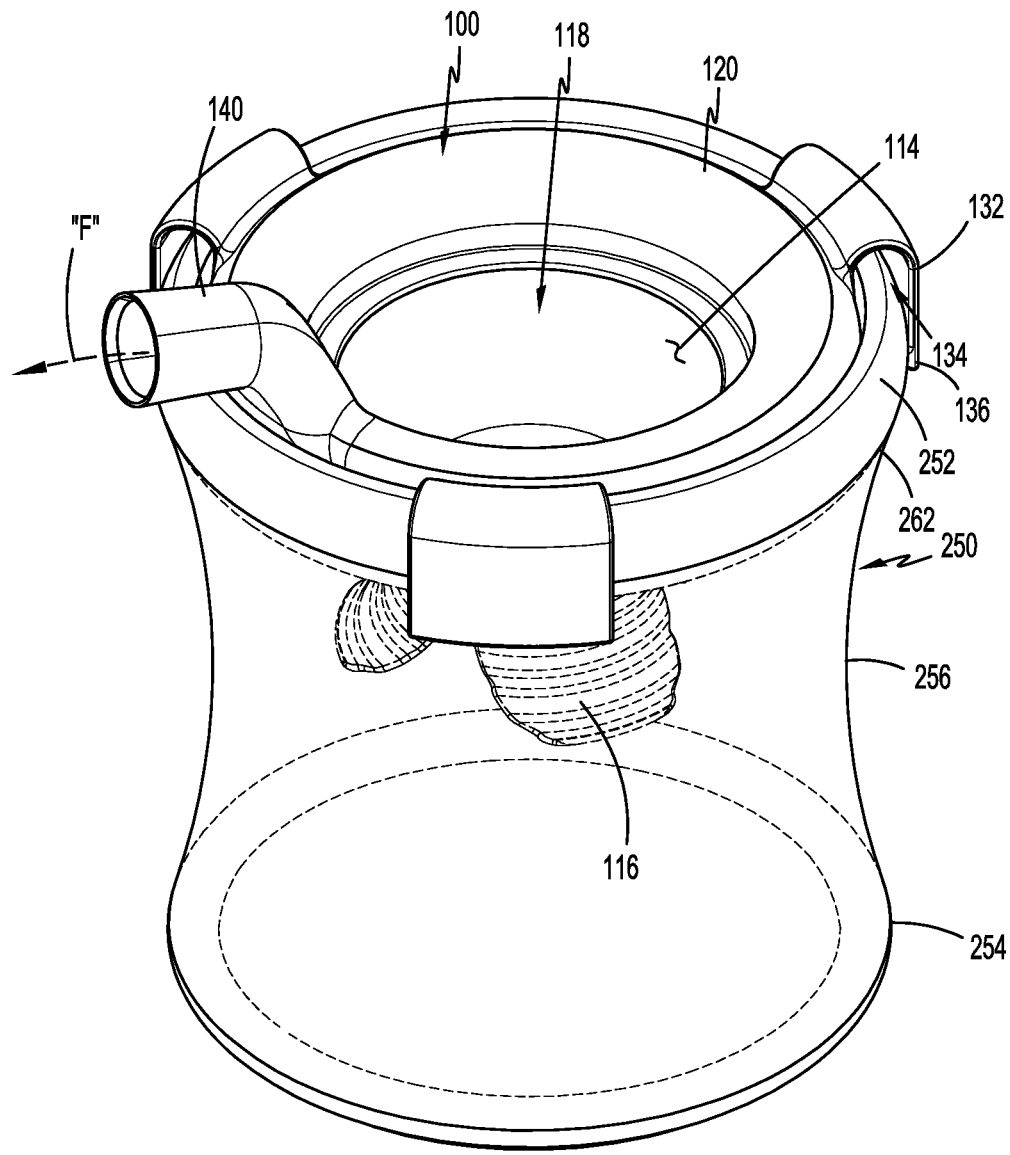
FIG. 4 is a top, perspective view of the system of FIG. 3 in an assembled state.

Referring to FIGS. 1 and 2, a smoke evacuating tissue guard provided in accordance with the present disclosure is shown generally identified by reference numeral 100. Smoke evacuating tissue guard 100 is formed from a suitable material, e.g., a biocompatible plastic such as, for example, polyethylene, polycarbonate, etc., from any suitable method, e.g., injection molding a single component or multiple components permanently secured or releasably engagable with one another. The material, thickness, and configuration of smoke evacuating tissue guard 100 (also referred to herein as "tissue guard 100") are selected such that tissue guard 100 defines sufficient stiffness to maintain its shape when positioned within an opening in tissue and/or when engaged within an access device 250 (FIGS. 3 and 4). However, the material, thickness, and configuration of tissue guard 100 also provide sufficient resilient flexibility to permit manipulation of tissue guard 100 from an at-rest position for insertion into an opening in tissue and/or for engagement within access device 250, with tissue guard 100 returning to or towards the at-rest position after insertion and/or engagement. Further, the material, thickness, and configuration of tissue guard 100 is selected such that tissue guard 100 is configured to withstand cutting and puncturing by surgical knives, scalpels, pencils, and the like, thereby protecting surrounding tissue and/or access device 250 from being cut or punctured. Tissue guard 100 may additionally or alternatively be configured to inhibit transfer of thermal and/or electrical energy therethrough to protect surrounding tissue and/or access device 250 from thermal and/or electrical energy.

Tissue guard 100 includes a tubular body 110, a collar 120 coupled to a proximal end portion 114 of tubular body 110, and an outlet 140 coupled to the collar 120 and configured to couple to a vacuum source (not shown). Tubular body 110, collar 120, and outlet 140 may be monolithically formed as a single component, e.g., via injection molding. Tubular body 110 defines open proximal end portion 114, an open distal end portion 116, and a passageway 118 extending therethrough between open proximal and distal end portions 114, 116, respectively. Passageway 118 is configured to receive one or more surgical instruments (not shown) therethrough. Proximal and distal end portions 114, 116 of tubular body 110 may each flare outwardly from an intermediate portion 122 of tubular body 110. More specifically, tubular body 110 may have an hourglass shape with a diameter of the open proximal and distal end portions 114, 116 thereof being greater than a diameter of tubular body 110 at intermediate portion 122 thereof. In aspects, proximal end portion 114 of tubular body 110 may assume a funnel-shape and may extend at an angle from about 15 degrees to about 50 degrees, and in some aspects about 17 degrees, from a longitudinal axis "X" defined by passageway 118.

Distal end portion 116 of tubular body 110 includes a plurality of segments 116a, 116b, 116c extending distally from intermediate portion 122. Each of segments 116a, 116b, 116c tapers (e.g., gradually narrow) in a distal direction, such that adjacent segments (e.g., segments 116a, 116b) define a cutout or gap 124 therebetween that increases in width in a distal direction. In aspects, cutout 124 defined between adjacent segments 116a, 116b has a rounded proximal end portion 124a whereas a remaining distal end portion 124b of cutout 124 has a generally triangular shape. Other shapes of the cutout 124 are also contemplated, such as, elongated, rectangular, rounded, or the like. In aspects, distal end portion 116 of tubular body 110 may be uninterrupted along its circumference, such that distal end portion 116 is without segments 116a, 116b, 116c or cutouts 124. Cutouts 124 facilitate flexion of distal end portion 116, e.g., to facilitate insertion into an opening in tissue and/or engagement within access device 250 (FIGS. 3 and 4). Each of segments 116a, 116b, 116c has an outer surface having a plurality of horizontally-extending ribs 126 configured to resist backing-out of tissue guard 100 from a surgical opening and/or access device 250 (FIGS. 3 and 4.)

Collar 120 of tissue guard 100 has a ring-shape and defines an annular channel 128 extending circumferentially about passageway 118 of tubular body 110. Annular channel 128 has a circular transverse cross-sectional shape (FIG. 2) having a diameter "D1." Collar 120 includes an outer annular half-section 120a and an inner annular half-section 120b integrally formed with one another and together defining annular channel 128. Outer annular half-section 120a extends directly from proximal end portion 114 of tubular body 110.

Inner annular half-section 120b of collar 120 extends directly from outer annular half-section 120a and into overlapping alignment with proximal end portion 114 of tubular body 110. Inner annular half-section 120a is spaced from proximal end portion 114 of tubular body 110. More specifically, inner annular half-section 120b has a bent inner edge 142 facing proximal end portion 114 of tubular body 110 to define a first annular gap "G1" therebetween. First annular gap "G1" extends circumferentially about passageway 118 and fluidly interconnects passageway 118 of tubular body 110 and annular channel 128 of collar 120. In aspects, inner annular half-section 120b may define a plurality of oval-shaped openings (not shown) circumferentially spaced from one another along collar 120. The openings are configured to establish fluid communication between passageway 118 and annular channel 128 and to reduce turbulence/noise.

Collar 120 further includes a lip 144 extending radially inward from bent inner edge 142 of inner annular half-section 120b of collar 120. Lip 144 may extend perpendicularly relative to longitudinal axis "X" of passageway 118. In aspects, lip 144 may extend relative to longitudinal axis "X" at any suitable angle. Lip 144 extends circumferentially about passageway 118, thereby defining an outer perimeter of passageway 118. Lip 144 defines a circumferential inner edge 146 that is spaced (in a direction generally parallel with longitudinal axis "X" of passageway 118) from proximal end portion 114 of tubular body 110 to define a second annular gap "G2" therebetween. First annular gap "G1" is sized to be less than diameter "D1" of annular channel 128 of collar 120 and second gap "G2." By making first annular gap "G1" less than second annular gap "G2" and diameter "D1," the Venturi Effect dictates that tissue guard 100 establishes a pressure differential in first annular gap "G1" upon application of suction through tissue guard 100, thereby making for a smoother and faster transition from passageway 118 to outlet 140 with minimal disruption of the flow of evacuated smoke.

Collar 120 may further include a plurality of hooks 132 projecting outwardly and ultimately distally from outer annular half-section 120a of collar 120. Each of hooks 132 has a proximal end portion 132a defining an arcuate aperture 134 configured to receive a proximal rim 252 (FIGS. 3 and 4) of access device 250, and a distal end portion 132b having an inwardly-projecting claw 136 configured to engage an undersurface or overhang 262 of proximal rim 252 of access device 250. In aspects, tissue guard 100 may be without hooks 132 and/or hooks 132 may be detachable from collar 120 for instances where tissue guard 100 is to be placed within a tissue opening without utilizing access device 250 (FIGS. 3 and 4.)

Outlet 140 of tissue guard 100 defines a tubular configuration, is formed with outer annular half-section 120a of collar 120, and extends radially outward from collar 120. In aspects, outlet 140 may extend proximally from collar 120 or may assume a helical configuration. Outlet 140 defines an internal channel 150 and has a first end portion 140a in fluid communication, e.g., via an aperture 148 defined through collar 120, with annular channel 128 of collar 120. Outlet 140 has a second end portion 140b configured to connect to tubing (not shown) of a vacuum source to enable smoke to be evacuated from an internal surgical site through a fluid path "F" (FIG. 2) that extends from passageway 118 of tubular body 110, into annular channel 128 via second annular gap "G2" and then first annular gap "G1," and, in turn, into inner channel 150 of outlet 140 via annular channel 128 upon application of suction through smoke evacuating tissue guard 100.

With reference to FIGS. 3 and 4, a system 200 provided in accordance with the present disclosure includes tissue guard 100 and access device 250. Access device 250 may be configured as a tissue retractor, an access port, or other suitable access device configured for positioning within an opening in tissue, e.g., a surgical incision or a naturally-occurring orifice, to provide access therethrough into an internal surgical site. Access device 250 includes proximal rim 252 configured for positioning on an external side of the opening in tissue, a distal rim 254 configured for positioning on an internal side of the opening in tissue, and a body 256 extending between proximal and distal rims 252, 254, respectively. Body 256 is configured to extend through the opening in tissue and defines a passageway 258 extending longitudinally therethrough to permit access to an internal surgical site through the opening in tissue. At least a portion of body 256 of access device 250 may be flexible to facilitate insertion and positioning of access device 250 within the opening in tissue. In aspects, body 256 is formed from a flexible sleeve of material including one or more layers of material. Further, access device 250 may be selectively adjustable, e.g., by rolling proximal rim 254 distally about body 256, to retract tissue and/or secure access device 250 within the opening in tissue. Access device 250 further defines overhang 262 between proximal rim 254 and body 256.

In use, access device 250 is positioned within an opening in tissue such that distal rim 254 is disposed on an internal surface of tissue on the internal side of the opening in tissue, body 256 extends through the opening in tissue, and proximal rim 252 is disposed on an exterior surface of tissue on the external side of the opening in tissue. Access device 250 may be adjusted to conform access device 250 to a patient's anatomy, retracting tissue and/or securing access device 250 within the opening in tissue.

With access device 250 disposed within the opening in tissue, tissue guard 100 is inserted into passageway 258 and hooks 132 of tissue guard 100 are flexed or otherwise manipulated to permit proximal rim 252 to be received in aperture 134 of hooks 132 and claw 136 of hooks 132 to engage overhang 262 of proximal rim 252, thereby locking tissue guard 100 in engagement within access device 250. With tissue guard 100 engaged within access device 250, surgical instrumentation may be inserted through passageway 118 of tubular body 110 of tissue guard 100 into the internal surgical site to, for example, extract a tissue specimen therefrom. Tissue guard 100, as noted above, protects tissue as well as access device 250 during the insertion, manipulation, use and withdrawal of any such surgical instrumentation.

It may be desirable to withdraw smoke or other fluid from the internal surgical site. For example, electrosurgical instrumentation may be utilized to electrically or electromechanically cut tissue to facilitate withdrawal of a tissue specimen, thereby generating smoke within the internal surgical site. In such instances, a source of suction may be attached to outlet 140 to establish suction through tissue guard 100. As such, surgical smoke within the surgical site is drawn into passageway 118 of tubular body 110, then into annular channel 128 of collar 120 via first and second annular gaps "G1," "G2," then into outlet 140, and then out of a clinician's view. Due to first annular gap "G1" having a reduced area relative to each of an area of second annular gap "G2" and a cross-sectional area of annular channel 128, first annular gap "G1" has a lower relative pressure, thereby making for a smoother and faster transition from passageway 118 to outlet 140 with minimal disruption of the flow of evacuated smoke. In aspects, a ratio of the area of the first annular gap "G1" to the area of the second annular gap "G2" to the cross-sectional area of the annular channel 128 may be about 1:2:4, and in some aspects, about 1:2.1:3.8.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A smoke evacuating tissue guard, comprising:
a tubular body having an outwardly flared proximal end portion and a distal end portion, the tubular body defining a longitudinally-extending passageway;
a collar attached to the proximal end portion of the tubular body and defining an annular channel, the collar including:
an outer annular section;
an inner annular section facing the passageway and spaced from the proximal end portion of the tubular body to define a first gap therebetween; and
a lip extending radially inward from the inner annular section and spaced from the proximal end portion of the tubular body to define a second gap therebetween; and
an outlet extending from the collar and defining an inner channel in fluid communication with the annular channel, wherein the first gap is less than a diameter of the annular channel and the second gap, such that the smoke evacuation tissue guard is configured to establish a pressure differential in the first gap upon application of suction through the smoke evacuating tissue guard.

2. The smoke evacuating tissue guard according to claim 1, wherein the lip extends perpendicular to a longitudinal axis defined by the passageway of the tubular body.

3. The smoke evacuating tissue guard according to claim 1, wherein the distal end portion of the tubular body is flared outwardly and includes a plurality of segments that taper in a distal direction, such that adjacent segments of the plurality of segments define a gap therebetween that increases in width in a distal direction.

4. The smoke evacuating tissue guard according to claim 1, further comprising a plurality of hooks coupled to the outer annular section of the collar and adapted to connect to a proximal rim of an access device.

5. The smoke evacuating tissue guard according to claim 1, wherein the first gap extends circumferentially about the passageway.

6. The smoke evacuating tissue guard according to claim 5, wherein the annular channel is in fluid communication with the passageway of the tubular body via the first and second gaps.

7. The smoke evacuating tissue guard according to claim 1, wherein the collar, the tubular body, and the outlet are monolithically formed with one another as a single component.

8. A smoke evacuating tissue guard, comprising:
a tubular body defining a longitudinally-extending passageway and including:
an outwardly flared proximal end portion;
an outwardly flared distal end portion; and
an intermediate portion connecting the proximal and distal end portions;
a ring-shaped collar defining an annular channel and including:
an outer annular section extending from the proximal end portion of the tubular body;
an inner annular section facing the passageway and being spaced from the proximal end portion of the tubular body to define a first annular gap therebetween; and
an outlet coupled to the collar and defining an inner channel in fluid communication with the annular channel, wherein the smoke evacuating guard is configured to establish a fluid path that extends from the passageway of the tubular body, into the annular channel via the first annular gap, and into the inner channel via the annular channel upon application of suction through the smoke evacuating tissue guard.

9. The smoke evacuating tissue guard according to claim 8, wherein the collar further includes a lip extending radially inward from the inner annular section.

10. The smoke evacuating tissue guard according to claim 9, wherein the lip is spaced from the proximal end portion of the tubular body to define a second annular gap therebetween.

11. The smoke evacuating tissue guard according to claim 10, wherein the first annular gap is less than a diameter of the annular channel and the second gap, such that the smoke evacuation tissue guard is configured to establish a pressure differential in the first annular gap upon application of suction through the smoke evacuating tissue guard.

12. The smoke evacuating tissue guard according to claim 9, wherein the lip extends perpendicular to a longitudinal axis defined by the passageway of the tubular body.

13. The smoke evacuating tissue guard according to claim 8, wherein the distal end portion of the tubular body includes a plurality of segments that taper in a distal direction, such that adjacent segments of the plurality of segments define a gap therebetween that increases in width in a distal direction.

14. The smoke evacuating tissue guard according to claim 8, further comprising a plurality of hooks coupled to the outer annular section of the collar and adapted to connect to a proximal rim of an access device.

15. The smoke evacuating tissue guard according to claim 8, wherein the first annular gap extends circumferentially about the passageway.

16. The smoke evacuating tissue guard according to claim 15, wherein the annular channel is in fluid communication with the passageway of the tubular body via the first and second annular gaps.

17. The smoke evacuating tissue guard according to claim 8, wherein the collar, the tubular body, and the outlet are monolithically formed with one another as a single component.

* * * * *